United States Patent
Giroud et al.

(10) Patent No.: US 7,850,950 B2
(45) Date of Patent: Dec. 14, 2010

(54) COMPOSITION FOR WASHING AND CONDITIONING KERATIN FIBERS, COMPRISING A PARTICULAR AMPHIPHILIC DIBLOCK COPOLYMER

(75) Inventors: Franck Giroud, Clichy (FR); Claude Dubief, le Chesnay (FR)

(73) Assignee: L'Oreal S.A., Paris (FR)

( * ) Notice: Subject to any disclaimer, the term of this patent is extended or adjusted under 35 U.S.C. 154(b) by 892 days.

(21) Appl. No.: 10/993,427

(22) Filed: Nov. 22, 2004

(65) Prior Publication Data
US 2005/0129647 A1 Jun. 16, 2005

Related U.S. Application Data

(60) Provisional application No. 60/529,752, filed on Dec. 17, 2003.

(30) Foreign Application Priority Data
Nov. 21, 2003 (FR) .................. 03 13631

(51) Int. Cl.
*A61K 8/00* (2006.01)
(52) U.S. Cl. .................. 424/70.1; 424/70.11
(58) Field of Classification Search .......... None
See application file for complete search history.

(56) References Cited

U.S. PATENT DOCUMENTS

| 2,528,378 | A | 10/1950 | Mannheimer |
| 2,781,354 | A | 2/1957 | Mannheimer |
| 6,297,203 | B1 | 10/2001 | Guskey et al. |
| 6,410,005 | B1 * | 6/2002 | Galleguillos et al. ..... 424/70.16 |
| 2003/0059392 | A1 | 3/2003 | L'Alloret |
| 2003/0223948 | A1 | 12/2003 | Maubru |

FOREIGN PATENT DOCUMENTS

FR 2 827 514 1/2003
GB 2 255 101 10/1992

OTHER PUBLICATIONS

Porter, M.R., *Handbook of Surfactants*, Blackie & Son: London, pp. 116-178 (1991).
T.P. Davis et al., "Recent Developments in Radical Polymerization," New Methods of Polymer Synthesis, vol. 2, 1995, pp. 1-36.
Craig J. Hawker, "Advances in 'Living' Free-Radical Polymerization: Architectural and Structural Control," Trends In Polymer Science, vol. 1, No. 6, Jun. 1996, pp. 183-188.
Jin-Shan Wang et al, "Controlled/'Living' radical Polymerication. Atom Transfer Radical Polymerization in the Presence of Transition-Metal Complexes," J. Am. Chem. Soc, vol. 117, 1995, pp. 5614-5615.
Michael K. Georges et al., "Narrow Molecular Weight Resins by a Free-Radical Polymerization Process," Macromolecules, vol. 26, 1993, pp. 2987-2988.
Notice of Opposition to European Patent Application No. 04 292 659.2, dated May 15, 2008, 8 pages.

* cited by examiner

*Primary Examiner*—Robert A Wax
*Assistant Examiner*—Bethany Barham
(74) *Attorney, Agent, or Firm*—Finnegan, Henderson Farabow, Garrett & Dunner, LLP

(57) ABSTRACT

The present invention relates to a composition for washing and conditioning keratin fibers, comprising, in a cosmetically acceptable medium: at least one washing base comprising at least one anionic surfactant, and at least one anionic or nonionic amphiphilic diblock copolymer, comprising a hydrophilic block and a hydrophobic block, other than a diblock copolymer of ethylene oxide and of propylene oxide, a urethane block copolymer and a siloxane block copolymer, where the amphiphilic diblock copolymer has a ratio of the number of monomer units in the hydrophilic block to the number of monomer units in the hydrophobic block ranging from 7 to 24.

The invention also relates to the method of using this composition for washing and conditioning keratin fibers, such as hair, and to a process for washing and conditioning keratin fibers using it.

33 Claims, No Drawings

COMPOSITION FOR WASHING AND CONDITIONING KERATIN FIBERS, COMPRISING A PARTICULAR AMPHIPHILIC DIBLOCK COPOLYMER

This application claims benefit of U.S. Provisional Application No. 60/529,752, filed Dec. 17, 2003, which is incorporated herein by reference.

Disclosed herein is a composition for washing and conditioning keratin fibers, comprising a washing base and a particular diblock copolymer as a conditioner. Also disclosed herein is a process for washing and conditioning keratin fibers, such as hair, using the composition.

In the field of conditioning shampoos, a washing base is generally combined with a conditioning agent, which may be a cationic polymer, an amphoteric polymer, a silicone, a synthetic or natural oil, a fatty substance, or a mixture thereof. These conditioners are typically used to improve disentangling of and softness of wet and dried hair, but may have a limited effect on hairstyle hold properties, and may make the hair lank and dull.

The use of amphiphilic block copolymers comprising hydrophilic and hydrophobic blocks is known in the cosmetics field. Specifically, European patent application EP 1,279,398 describes the use of such copolymers as gelling agents in aqueous cosmetic compositions.

The present inventors, however, have discovered that the use of some of these amphiphilic block copolymers with a washing base makes it possible to overcome at least one of the drawbacks listed above that may be encountered with standard conditioners, and thus to obtain an improved hair conditioner composition. This use of amphiphilic block copolymers provides at least one desirable hair conditioning property, such as improved disentangling of and softness of wet hair, and disentangling of, hold, liveliness, and sheen of dried hair, that may be greatly improved over these properties seen with standard conditioners.

Therefore, one aspect of the present disclosure is a composition for washing and conditioning keratin fibers, comprising a washing base and, as a conditioner, at least one anionic or nonionic amphiphilic diblock copolymer as described below.

Another aspect of the present disclosure relates to a process for washing and conditioning keratin fibers, such as hair, using the composition disclosed herein.

Other subjects, characteristics, aspects, and advantages of the present disclosure will be elucidated upon reading the description provided below and the examples that follow.

In one aspect, the present disclosure relates to a composition for washing and conditioning keratin fibers comprising, in a cosmetically acceptable medium:
(1) at least one washing base comprising at least one anionic surfactant, and
(2) at least one amphiphilic diblock copolymer chosen from anionic and nonionic amphiphilic diblock copolymers, comprising a hydrophilic block and a hydrophobic block,
wherein said at least one amphiphilic diblock copolymer is other than a diblock copolymer of ethylene oxide and of propylene oxide, a urethane block copolymer, and a siloxane block copolymer; and
wherein, said at least one amphiphilic diblock copolymer has a ratio of the number of monomer units in the hydrophilic block to the number of monomer units in the hydrophobic block ranging from about 7 to 24.

As used herein, the term "hydrophobic block" means a polymer block comprising at least 80 mol % of at least one water-insoluble monomer, and up to 20 mol % of at least one water-soluble monomer as described below. The at least one water-soluble monomer is randomly distributed within the hydrophobic block. In some embodiments, the amount of the at least one water-soluble monomer used may be equal to or less than 10 mol %, or equal to or less than 5 mol %.

Alternatively, the hydrophobic block may be formed solely from at least one water-insoluble monomer, and need not contain any water-soluble monomers.

In one embodiment, the hydrophobic block may have a glass transition temperature (Tg) of greater than 30° C., or, in other embodiments, the Tg may be greater than 80° C. Tg may be measured by differential scanning calorimetry (DSC) on a sample of from 5 to 15 mg of polymer under nitrogen, while following a temperature gradient of 10° C. per minute on the homopolymer or the copolymer formed from the monomer(s) of the hydrophobic block. Tg may also be measured directly by DSC on a sample of the diblock copolymer of the invention.

The at least one water-insoluble monomer forming the hydrophobic block of the amphiphilic diblock copolymers may be chosen from alkylated and non-alkylated vinyl aromatic monomers such as styrene and alkylated styrenes, for example, 4-butylstyrene, α-methylstyrene, and vinyltoluene; dienes such as butadiene and 1,3-hexadiene; and alkylated dienes, such as isoprene and dimethylbutadiene; chloroprene; $C_{1-10}$ alkyl, $C_{6-10}$ aryl, or $C_{6-10}$ aralkyl acrylates and $C_{1-10}$ alkyl, $C_{6-10}$ aryl, methacrylates, such as methyl, ethyl, n-butyl, 2-ethylhexyl, tert-butyl, isobornyl, phenyl, and benzyl (meth)acrylates; vinyl acetate; the vinyl ethers of formula $CH_2=CH-O-R$ and the allyl ethers of formula $CH_2=CH-CH_2-O-R$, wherein R is a $C_{1-6}$ alkyl group; acrylonitrile; vinyl chloride; vinylidene chloride; caprolactone; ethylene; propylene; and vinyl monomers that are fluorinated or that contain a perfluoro chain, such as fluoroalkyl acrylates or methacrylates, or alkyl α-fluoroacrylates.

In one embodiment, the at least one water-insoluble monomer forming the hydrophobic block may be chosen from vinyl aromatic compounds such as styrene, 4-butylstyrene, (α-methylstyrene, and vinyltoluene. For example, the water-insoluble monomer may be styrene.

The term "hydrophilic block," as used herein, means a polymer block comprising at least 80 mol % of at least one water-soluble monomer, and up to 20 mol % of at least one water-insoluble monomer as defined above, wherein the at least one water-insoluble monomer is randomly distributed in the hydrophilic block. In other embodiments, the proportion of water-insoluble monomers in the hydrophilic block may be up to 10 mol %, or equal to or less than 5 mol %. Alternatively, the hydrophilic block may be formed solely from at least one water-soluble monomer.

The at least one water-soluble monomer forming the hydrophilic block of the amphiphilic diblock copolymers used herein may be anionic or nonionic in nature.

Anionic water-soluble monomers that may be used herein include, for example, ethylenically unsaturated carboxylic acids, such as acrylic acid, (meth)acrylic acid, itaconic acid, fumaric acid, crotonic acid and maleic acid; 2-acrylamido-2-methylpropanesulfonic acid; styrenesulfonic acid; vinylsulfonic acid, and vinylphosphonic acid; and salts thereof, such as sodium, potassium, or ammonium salts.

In one embodiment, the at least one water-soluble monomer may be (meth)acrylic acid or its salts. In another embodiment, it may be acrylic acid or its salts. Nonionic water-soluble monomers that may be used herein include, for example, acrylamide, N—($C_{1-6}$alkyl)- or N,N-di($C_{1-3}$ alkyl)-acrylamides, polyethylene glycol acrylate, polyethylene glycol methacrylate, N-vinylacetamide, N-methyl-N-vinylacetamide, N-vinylformamide, N-methyl-N-vinylformamide, N-vinyllactams comprising a cyclic group of 4 to 9 carbon atoms, vinyl acetate and then hydrolysed), ethylene oxide, hydroxyethyl acrylate, hydroxypropyl acrylate, hydroxyethyl methacrylate, and hydroxypropyl methacrylate.

As previously noted, the ratio of the number of monomer units in the hydrophilic block to the number of monomer units in the hydrophobic block can range from 7 to 24. In other embodiments, the ratio can range from 8 to 20, or 12 to 20.

The total weight-average molecular weight of the amphiphilic diblock copolymer ranges from 500 to 100,000, and in some embodiments ranges from 1,000 to 60,000, or 10,000 to 60,000. In some embodiments, the amphiphilic diblock copolymers that may be used are diblock polymers of acrylic acid or a salt thereof, and of styrene. The amphiphilic diblock copolymers may be soluble or dispersible in the aqueous medium. In one embodiment, the amphiphilic diblock copolymer is water-soluble.

As used herein, the term "water-soluble compound" means a compound (polymer or monomer) which, when introduced into water at 25° C., and neutralized if necessary, at a weight concentration equal to 0.1%, makes it possible to obtain a solution or suspension that is macroscopically homogeneous and transparent. A solution or suspension that is macroscopically homogeneous and transparent has a light transmittance value of at least 70% or at least 80% at a wavelength equal to 500 nm, through a sample 1 cm thick.

The block polymers used herein may be prepared by synthetic processes conventionally used for obtaining block polymers. Such synthetic processes include, e.g., anionic polymerization and controlled free-radical polymerization (see "New Method of Polymer Synthesis," Blackie Academic & Professional, London, Vol. 2, p. 1 (1995) or C. J. Hawker, Trends Polym. Sci. 4, p. 183 (1996)), which may be used in various processes such as atom transfer radical polymerization (ATRP) (see Matyjasezwski et al., JACS, Vol. 117, p. 5614 (1995)), and a method with free radicals such as nitroxides (Georges et al., Macromolecules, 26, 2987 (1993)).

These processes may be used to obtain only one of the two types of blocks in the polymer disclosed herein, the other block being introduced into the final polymer by means of an initiator, or alternatively, via a coupling reaction between the hydrophilic and hydrophobic blocks.

The at least one amphiphilic diblock copolymer may be present in the composition in an amount ranging from 0.01% to 30% by weight, or, in other embodiments, in amounts ranging from 0.05% to 10% by weight, or from 0.1% to 5% by weight relative to the total weight of the composition.

The washing and foaming base used in the composition according to the invention comprises at least one anionic surfactant. It may also comprise at least one nonionic surfactant and/or at least one amphoteric surfactant.

The amount of washing base, i.e., the total amount of surfactants, may be from 4% to 50% by weight and in some embodiments of the invention, from 5% to 20% by weight relative to the total weight of the composition.

The anionic surfactants useful in the compositions disclosed herein may be chosen from salts, for example alkali metal salts such as sodium salts, ammonium salts, amine salts, amino alcohol salts, and alkaline-earth metal salts, for example magnesium salts, of the following types: alkyl sulfates, alkyl ether sulfates, alkylamido ether sulfates, alkylarylpolyether sulfates, monoglyceride sulfates, alkyl sulfonates, alkylamide sulfonates, alkylaryl sulfonates, α-olefin sulfonates, paraffin sulfonates, alkyl sulfosuccinates, alkyl ether sulfosuccinates, alkylamide sulfosuccinates, alkyl sulfoacetates, acyl sarcosinates, and acyl glutamates, wherein the alkyl and acyl groups of all these anionic surfactant salt compounds contain from 6 to 24 carbon atoms, and the aryl group may be a phenyl or benzyl group.

It is also possible to use $C_{6-24}$ alkyl monoesters of polyglycoside-dicarboxylic acids as anionic surfactants, such as alkyl glucoside-citrates, alkyl polyglycoside tartrates and alkyl polyglycoside sulfosuccinates, alkyl sulfosuccinamates, acylisethionates and N-acyltaurates, wherein the alkyl or acyl group of all these compounds contains from 12 to 20 carbon atoms.

Another group of anionic surfactants that may be used in the compositions disclosed herein is the acyl lactylates group, in which the acyl group contains from 8 to 20 carbon atoms.

In addition, mention may also be made of alkyl-D-galactoside-uronic acids and salts thereof, polyoxyalkylenated ($C_{6-24}$ alkyl)ether-carboxylic acids, polyoxyalkylenated ($C_{6-24}$ alkyl)($C_{6-24}$ aryl)ether-carboxylic acids, and polyoxyalkylenated ($C_{6-24}$ alkyl)amidoether-carboxylic acids and salts thereof, such as those comprising from 2 to 50 ethylene oxide units, and mixtures thereof.

Further, alkyl sulfates, alkyl ether sulfates, alkyl ether carboxylates, and mixtures thereof may also be used as anionic surfactants, such as in the form of alkali metal, alkaline-earth metal, ammonium, amine, or amino alcohol salts.

The at least one anionic surfactant used herein may be present in a total amount ranging from 1% to 50% by weight relative to the total weight of the composition. In some embodiments, the at least one anionic surfactants is present in a total amount ranging from 4% to 50% by weight or from 4% to 20% by weight.

The nonionic surfactants that may be used herein are compounds that are well-known (see M. R. Porter, "Handbook of Surfactants," Blackie & Son, published in Glasgow and London, pp. 116-178 (1991)). The nonionic surfactants may be chosen from polyethoxylated, polypropoxylated or polyglycerolated fatty acids, ($C_1$-$C_{20}$)alkylphenols, α-diols or alcohols having a fatty chain containing, e.g., 8 to 18 carbon atoms, wherein it is possible that the number of ethylene oxide or propylene oxide groups can range from 2 to 50, and the number of glycerol groups can range from 2 to 30.

Mention may also be made of condensates of ethylene oxide and of propylene oxide with fatty alcohols, polyethoxylated fatty amides comprising 2 to 30 ethylene oxide units, polyglycerolated fatty amides comprising 1 to 5 or 1.5 to 4 glycerol groups, ethoxylated fatty acid esters of sorbitan comprising 2 to 30 mol of ethylene oxide, fatty acid esters of sucrose, fatty acid esters of polyethylene glycol, ($C_{6-24}$ alkyl) polyglycosides, N—($C_{6-24}$ alkyl)glucamine derivatives, and amine oxides such as ($C_{10}$-$C_{14}$)alkylamine oxides or N—($C_{10-14}$ acyl)aminopropylmorpholine oxides.

In one embodiment, the at least one nonionic surfactant is chosen from ($C_{6-24}$ alkyl)polyglycosides.

The amphoteric surfactants that may be used herein include tertiary or secondary aliphatic amine derivatives in which the aliphatic group is a linear or branched chain containing from 8 to 22 carbon atoms and containing at least one anionic group (for example, carboxylate, sulfonate, sulfate, phosphate, or phosphonate). In some embodiments, the amphoteric surfactants that may be used include ($C_8$-$C_{20}$) alkylbetaines, sulfobetaines, ($C_8$-$C_{20}$)alkylamido($C_6$-$C_8$) alkylbetaines, or ($C_8$-$C_{20}$)alkylamido($C_6$-$C_8$)alkylsulfobetaines.

Among the amine derivatives, mention may be made of the products sold under the name Miranol®, as described in U.S. Pat. Nos. 2,528,378 and 2,781,354 and classified in the CTFA dictionary, 3rd edition, 1982, under the names amphocarboxyglycinate and amphocarboxypropionate, having the respective structures (1) and (2):

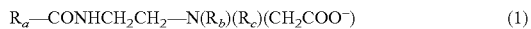
$$R_a\text{—CONHCH}_2\text{CH}_2\text{—N}(R_b)(R_c)(\text{CH}_2\text{COO}^-) \quad (1)$$

wherein
  $R_a$ is an alkyl group derived from an acid $R_a$—COOH present in hydrolysed coconut oil, a heptyl, nonyl or undecyl group;
  $R_b$ is a β-hydroxyethyl group; and
  $R_c$ is a carboxymethyl group; and

$$R_a{'}\text{—CONHCH}_2\text{CH}_2\text{—N(B)(C)} \quad (2)$$

wherein
  B is —CH$_2$CH$_2$OX';
  C is —(CH$_2$)$_z$—Y', where z=1 or 2;
  X' is —CH$_2$CH$_2$—COOH or a hydrogen atom;
  Y' is —COOH or —CH$_2$—CHOH—SO$_3$H; and
  $R_a{'}$ is an alkyl group derived from an acid $R_a{'}$—COOH present in hydrolyzed coconut oil or in hydrolyzed linseed oil, an alkyl group such as a $C_{17}$ alkyl group and its isoform, and an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylampho-dipropionate, disodium capryloamphodipropionate, lauroamphodipropionic acid, and cocoamphodipropionic acid. In one embodiment, the amphoteric surfactant used may be cocoamphodiacetate, sold by the company Rhodia under the trade name Miranol® C2M concentrate.

Among the amphoteric surfactants mentioned above, ($C_{8-20}$ alkyl)betaines, ($C_{8-20}$ alkyl)amido($C_{6-8}$ alkyl)betaines, alkylamphodiacetates, and mixtures thereof may be used, for example.

The nonionic and/or amphoteric surfactants may be present in the compositions disclosed herein in an amount ranging from 0% to 20% by weight, from 0.5% to 20% by weight, or from 0.5% to 10% by weight relative to the total weight of the composition.

As used herein, the term "cosmetically acceptable medium" means a medium that is compatible with keratin fibers such as hair, but which also has a pleasant odor, appearance, and feel.

A cosmetically acceptable aqueous medium comprises water or a mixture of water and of at least one organic solvent chosen from $C_1$-$C_4$ lower alcohols, such as ethanol, isopropanol, tert-butanol, or n-butanol, and polyols, such as glycerol, propylene glycol, and polyethylene glycols.

The pH of the composition of the present disclosure generally ranges from 2 to 11, such as from 3 to 10, or from 4 to 8.

The compositions disclosed herein may also include additives chosen from, for example, anionic and nonionic film-forming polymers other than the diblock polymers of the invention, cationic or amphoteric conditioning polymers, linear, branched, or cyclic volatile or non-volatile organomodified or non-organomodified silicones, associative or non-associative polymeric thickeners, non-polymeric thickeners, nacreous agents, opacifiers, colorants or pigments, fragrances, mineral, plant, or synthetic oils, waxes, vitamins, UV-screening agents, free-radical scavengers, antidandruff agents, preserving agents, pH stabilizers, solvents, and mixtures thereof.

Persons skilled in the art will have the ability to select the optional additives and the amount thereof such that they do not harm the desirable and beneficial properties of the composition disclosed herein. But generally, these additives are present in the compositions disclosed herein in an amount ranging from 0% to 20% by weight relative to the total weight of the composition.

Also disclosed herein is a process for washing and conditioning hair, which comprises the application of an effective amount of the composition described above to hair, and rinsing the composition after an optional leave-in time.

The examples that follow include illustrations of the present invention, and are not meant to be limitations on the scope of the invention in any manner. Unless otherwise indicated, all the amounts indicated are expressed as percentages by weight.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

EXAMPLES

The compositions of Examples 1 to 5 were prepared from the ingredients listed in Tables 1 and 2 below. The compositions of Examples 1 and 2 (Table 1) are compositions prepared for comparative purposes, while the compositions of Examples 3 to 5 (Table 2) are compositions of the present invention.

TABLE 1

| EXAMPLES (COMPARATIVE) | | 1 | 2 |
|---|---|---|---|
| Sodium lauryl ether sulfate (2.2 mol of ethylene oxide (EO)) | | 12.5%* | 12.5%* |
| Cocoylamidobetaine | | 2.5%* | 2.5%* |
| Polystyrene/poly(sodium acrylate) random copolymer | | — | 1.0% |
| Water | qs | 100.0% | 100.0% |
| pH with NaOH | | 7.0 | 7.0 |

*indicates Active Material

TABLE 2

| EXAMPLES (ACCORDING TO THE INVENTION) | 3 | 4 | 5 |
|---|---|---|---|
| Sodium lauryl ether sulfate (2.2 mol EO) | 12.5%* | 12.5%* | 12.5%* |
| Cocoylamidobetaine | 2.5%* | 2.5%* | 2.5%* |
| Polystyrene (2000 g/mol)/poly(sodium acrylate) | 1.0% | — | — |

TABLE 2-continued

| EXAMPLES (ACCORDING TO THE INVENTION) | 3 | 4 | 5 |
|---|---|---|---|
| (14 000 g/mol) Polystyrene (2000 g/mol)/poly(sodium acrylate) (30 000 g/mol) | — | 1.0% | — |
| Polystyrene (2000 g/mol)/poly(sodium acrylate) (43 000 g/mol) | — | — | 1.0% |
| Water | qs 100.0% | 100.0% | 100.0% |
| pH | 7.0 | 7.0 | 7.0 |

*indicates Active Material

The compositions of the five examples were applied to locks of bleached hair. After working into a lather, they were rinsed and half the locks were dried.

The wet and dry locks were then given to experts for evaluation of the cosmetic properties of each of them.

The compositions of Examples 3 to 5 made it possible to obtain a better feel, better disentangling of, and improved sheen of the hair compared with the compositions of Examples 1 and 2. Particularly desirable cosmetic properties were obtained with the composition of Example 4.

What is claimed is:

1. A composition for washing and conditioning keratin fibers, comprising, in a cosmetically acceptable medium:
   (a) at least one washing base comprising at least one anionic surfactant; and
   (b) at least one amphiphilic diblock copolymer chosen from anionic and nonionic amphiphilic diblock copolymers, comprising a hydrophilic block and a hydrophobic block,
   wherein the hydrophobic block comprises at least 80 mol % of at least one water-insoluble monomer;
   wherein said at least one amphiphilic diblock copolymer is not a diblock copolymer of ethylene oxide and of propylene oxide, a urethane block copolymer, or a siloxane block copolymer;
   wherein said at least one amphiphilic diblock copolymer has a ratio of the number of monomer units in the hydrophilic block to the number of monomer units in the hydrophobic block ranging from 7 to 24; and
   wherein the amount of the at least one washing base ranges from 4% to 50% by weight, relative to the total weight of the composition.

2. The composition of claim 1, wherein the glass transition temperature of the hydrophobic block is greater than 30° C.

3. The composition of claim 2, wherein the glass transition temperature of the hydrophobic block is greater than 80° C.

4. The composition of claim 1, wherein the ratio of the number of monomer units in the hydrophilic block to the number of monomer units in the hydrophobic block ranges from 8 to 20.

5. The composition of claim 4, wherein the ratio of the number of monomer units in the hydrophilic block to the number of monomer units in the hydrophobic block ranges from 12 to 20.

6. The composition of claim 1, wherein the total weight-average molecular weight of said at least one amphiphilic diblock copolymer ranges from 500 to 100,000.

7. The composition of claim 6, wherein the total weight-average molecular weight of said at least one amphiphilic diblock copolymer ranges from 1,000 to 60,000.

8. The composition of claim 7, wherein the total weight-average molecular weight of said at least one amphiphilic diblock copolymer ranges from 10,000 to 60,000.

9. The composition of claim 1, wherein the hydrophobic block comprises up to 20 mol % of at least one water-soluble monomer.

10. The composition of claim 9, wherein the hydrophobic block comprises up to 10 mol % of at least one water-soluble monomer.

11. The composition of claim 10, wherein the hydrophobic block comprises up to 5 mol % of at least one water-soluble monomer.

12. The composition of claim 1, wherein the at least one water-insoluble monomer is chosen from alkylated and non-alkylated vinyl aromatic monomers; alkylated and non-alkylated dienes; chloroprene; C1-10 alkyl, C6-10 aryl, and C6-10 aralkyl acrylates; C1-10 alkyl, C6-10 aryl, and C6-10 aralkyl methacrylates; vinyl acetate; vinyl ethers of formula CH2=CH—O—R; and allyl ethers of formula CH2=CH—CH2—O—R wherein R is chosen from a C1-6 alkyl group, acrylonitrile, vinyl chloride, vinylidene chloride, caprolactone, ethylene, propylene, and vinyl monomers that are fluorinated or that contain a perfluoro chain.

13. The composition of claim 1, wherein the at least one water-insoluble monomer forming the hydrophobic block is chosen from styrene, 4-butylstyrene, α-methylstyrene, and vinyltoluene.

14. The composition of claim 1, wherein the hydrophilic block comprises at least 80 mol % of at least one water-soluble monomer chosen from anionic and nonionic water-soluble monomers.

15. The composition of claim 14, wherein the hydrophilic block comprises up to 20 mol % of at least one water-insoluble monomer.

16. The composition of claim 15, wherein the hydrophilic block comprises up to 10 mol % of at least one water-insoluble monomer.

17. The composition of claim 16, wherein the hydrophilic block comprises up to 5 mol % of at least one water-insoluble monomer.

18. The composition of claim 14, wherein the anionic water-soluble monomers are chosen from ethylenically unsaturated carboxylic acids, 2-acrylamido-2-methylpropanesulfonic acid, styrenesulfonic acid, vinylsulfonic acid and vinylphosphonic acid, and salts thereof.

19. The composition of claim 18, wherein the anionic water-soluble monomer is (meth)acrylic acid or a salt thereof.

20. The composition of claim 14, wherein the nonionic water-soluble monomers are chosen from acrylamide, N—(C1-6 alkyl)- or N,N-di(C1-3 alkyl)-acrylamides, polyethylene glycol acrylate, polyethylene glycol methacrylate, N-vinylacetamide, N-methyl-N-vinylacetamide, N-vinylformamide, N-methyl-N-vinyl-formamide, N-vinyllactams comprising a cyclic group of 4 to 9 carbon atoms, vinyl alcohol, ethylene oxide, hydroxyethyl acrylate, hydroxypropyl acrylate, hydroxyethyl methacrylate, and hydroxypropyl methacrylate.

21. The composition of claim 1, wherein the at least one amphiphilic diblock copolymer is present in an amount ranging from 0.01% to 30% by weight relative to the total weight of the composition.

22. The composition of claim 21, wherein the at least one amphiphilic diblock copolymer is present in an amount ranging from 0.05% to 10% by weight relative to the total weight of the composition.

23. The composition of claim 22, wherein the at least one amphiphilic diblock copolymer is present in an amount ranging from 0.1% to 5% by weight relative to the total weight of the composition.

24. The composition of claim 1, wherein the composition further comprises at least one additional surfactant chosen from non-ionic surfactants and amphoteric surfactants.

25. The composition of claim 1, wherein the at least one anionic surfactant is chosen from alkyl sulfates, alkyl ether sulfates and alkyl ether carboxylates.

26. The composition of claim 1, wherein the at least one anionic surfactant is chosen from alkali metal, alkaline-earth metal, ammonium, amine, and amino alcohol salts of alkyl sulfates, alkyl ether sulfates and alkyl ether carboxylates.

27. The composition of claim 24, wherein the non-ionic surfactants are chosen from ($C_{6-24}$alkyl)polyglycosides.

28. The composition of claim 24, wherein the amphoteric surfactants are chosen from ($C_{8-20}$alkyl)betaines, ($C_{8-20}$alkyl)amido($C_{6-8}$alkyl)betaines, alkylamphodiacetates, and mixtures thereof.

29. The composition of claim 24, wherein the at least one additional surfactant is present in a total amount ranging from 0% to 20% by weight relative to the total weight of the composition.

30. The composition of claim 29, wherein the at least one additional surfactant is present in a total amount ranging from 0.5% to 20% by weight relative to the total weight of the composition.

31. The composition of claim 1, wherein the cosmetically acceptable medium comprises water or a mixture of water and of at least one organic solvent.

32. The composition of claim 31, wherein the at least one organic solvent is chosen from $C_1$-$C_4$ lower alcohols and polyols.

33. The composition of claim 1, further comprising at least one additional ingredient chosen from anionic and nonionic film-forming polymers other than the at least one diblock polymer of claim 1, cationic and amphoteric conditioning polymers, linear, branched and cyclic, volatile and non-volatile organomodified and non-organomodified silicones, associative and non-associative polymeric thickeners, non-polymeric thickeners, nacreous agents, opacifiers, colorants and pigments, fragrances, mineral, plant and synthetic oils, waxes, vitamins, UV-screening agents, free-radical scavengers, antidandruff agents, preserving agents, pH stabilizers, solvents, and mixtures thereof.

* * * * *